United States Patent [19]

Hays et al.

[11] Patent Number: 5,955,472
[45] Date of Patent: Sep. 21, 1999

[54] NAPHTHYLAZO INHIBITION OF AMYLOIDOSIS

[75] Inventors: Sheryl Jeanne Hays; Harry LeVine, III, both of Ann Arbor; Jeffery David Scholten, Brighton, all of Mich.

[73] Assignee: Warner-Lambert Company, Morris Plains, N.J.

[21] Appl. No.: 09/066,397

[22] PCT Filed: Oct. 18, 1996

[86] PCT No.: PCT/US96/16747

§ 371 Date: Apr. 29, 1998

§ 102(e) Date: Apr. 29, 1998

[87] PCT Pub. No.: WO97/16194

PCT Pub. Date: May 9, 1997

Related U.S. Application Data

[60] Provisional application No. 60/006,230, Nov. 2, 1995.
[51] Int. Cl.$^6$ .......................... A01N 43/42; C07C 245/00
[52] U.S. Cl. ............................................. 514/310; 534/573
[58] Field of Search ............................. 514/310; 534/573

[56] References Cited

U.S. PATENT DOCUMENTS 3,218,309  11/1965  Elslager et al. ........................ 260/152

FOREIGN PATENT DOCUMENTS

| WO 94/01116 | 1/1994 | WIPO . |
| WO 94/09155 | 4/1994 | WIPO . |
| WO 94/09364 | 4/1994 | WIPO . |
| WO 94/13798 | 6/1994 | WIPO . |
| WO 95/06456 | 3/1995 | WIPO . |
| WO 95/06470 | 3/1995 | WIPO . |

OTHER PUBLICATIONS

International Search Report PCT/US 96/16747.

Eislager et al; CA; vol. 64; p 19509, (1966) month not available.

*Primary Examiner*—Louise N. Leary
*Attorney, Agent, or Firm*—Charles W. Ashbrook

[57] ABSTRACT

Amyloid aggregation in animals is inhibited by administering a naphthylazo compound of formula (I), wherein R1 and R2 are hydrogen, alkyl, substituted alkyl, or complete a heterocyclic ring, R3 is hydrogen or alkyl, R4, R5, R6, and R7 are substitutent groups. The compounds are especially useful in preventing and treating Alzheimer's disease.

8 Claims, No Drawings

NAPHTHYLAZO INHIBITION OF AMYLOIDOSIS

This application claims benefit of provisional application Se. No. 60/006,230 filed Nov. 2, 1995.

FIELD OF THE INVENTION

This invention concerns a method for inhibiting amyloidosis utilizing naphthylazo compounds. The invention is a method for diagnosing and treating diseases characterized by amyloidosis.

BACKGROUND OF THE INVENTION

Amyloid plaque formation is found in a number of diseases, including Alzheimer's disease, scrapie, bovine spongiform encephalophy, Gerstmann-Straussler Syndrome, and the like. The amyloid plaques comprise proteins bound together in a fibrinous matrix. Amyloidosis is the general name given to diseases and conditions characterized by the presence of amyloid protein. A number of different types of amyloid protein are known, and all types are considered pathological, since no normally occurring amyloids are known. Accordingly, the presence of amyloid protein in a host is an indication of abnormal formation of fibrils and plaques. Amyloidosis has been clinically observed in a number of disease states, including certain mental illnesses, neurological diseases, and collagenosis. Indeed, the brains of subjects diagnosed with Alzheimer's disease have one thing in common, namely an abundance of amyloid in the form of plaques and tangles.

Alzheimer's disease is a degenerative brain disorder characterized clinically by progressive loss of memory, cognition, reasoning, judgement, and emotional stability that gradually leads to mental deterioration and ultimately death. To date, only one clinically approved treatment is available, namely tacrine hydrochloride (Cognex®, from the Parke-Davis Division of Warner-Lambert Company). Because Alzheimer's disease and related degenerative brain disorders are a major medical issue for an aging population, the need for new treatments and methods for diagnosing the disorders are needed.

WO 9401116 describes the use of congo red, a biphenyl naphthylazo dye, to treat amyloidogenic diseases. We have now discovered that certain naphthylazo compounds inhibit amyloid aggregation for better than congo red. The naphthylazo compounds to be utilized in this invention are described as antiparasitic agents by Elslager, et al., in U.S. Pat. No. 3,218,309, which is incorporated herein by reference for its teaching of synthesis.

SUMMARY OF THE INVENTION

This invention provides a method for inhibiting amyloid aggregation in a mammal by administering a naphthylazo compound. More particularly, the invention is a method for preventing amyloidosis comprising administering to a mammal an effective amount of a compound having the formula

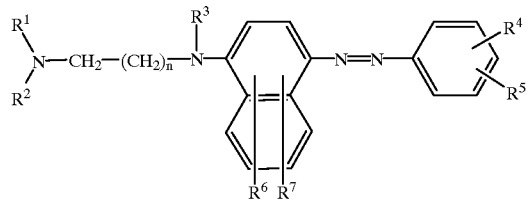

wherein:
$R^1$ and $R^2$ independently are hydrogen, $C_1$–$C_4$ alkyl, hydroxy $C_1$–$C_4$ alkyl, $C_1$–$C_4$ alkoxy-$C_2$–$C_4$ alkyl, $C_3$–$C_6$ cycloalkyl, or $R^1$ and $R^2$ taken together with the nitrogen to which they are attached complete a heterocyclic ring having from 4 to 12 carbon atoms;
n is 1, 2, or 3;
$R^3$ is hydrogen or $C_1$–$C_4$ alkyl;
$R^4$ and $R^5$ independently are hydrogen, hydroxy, halo, $C_1$–$C_4$ alkyl, $C_1$–$C_4$ alkoxy, phenoxy, benzyloxy, hydroxy-$C_1$–$C_4$ alkyl, hydroxy-$C_1$–$C_4$ alkoxy, $NR^1R^2$, $SO_2NR^1R^2$, $R^1R^2N$—$CH_2(CH_2)_n$—(O or NH)$_m$ where $R^1$, $R^2$, and n are as defined above, and m is 0 or 1, and $R^4$ and $R^5$ when attached to adjacent carbon atoms can be

$R^6$ and $R^7$ independently are hydrogen, hydroxy, halo, $C_1$–$C_4$ alkyl, $C_1$–$C_4$ alkoxy, or $R^1R^2N$-$CH_2(CH_2)_n$—(O or NH)$_m$—where $R^1$, $R^2$, m, and n are as defined above; and the pharmaceutically acceptable acid addition salts thereof.

In a preferred embodiment, the amyloid aggregation inhibitors utilized have the formula

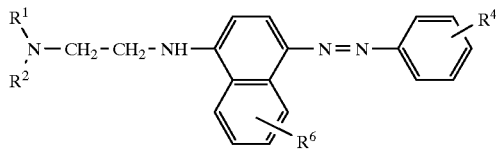

where $R^1$ and $R^2$ independently are $C_1$–$C_4$ alkyl and $R^4$ is hydrogen, halo, $SO_2NH_2$, benzyloxy, hydroxy $C_1$–$C_4$ alkyl, $NR^1R^2$, or $R^1R^2N$—$CH_2(CH_2)_n$—(O or NH)$_m$—, and $R^4$ is hydrogen or $C_1$–$C_4$ alkoxy.

In a further preferred embodiment, the amyloid aggregation inhibitors utilized have the formula

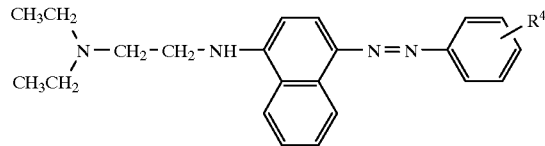

where $R^4$ is hydrogen, 3-chloro, 4-fluoro, benzyloxy, 2-(N,N-diethylamino)ethoxy, 2-hydroxyethoxy, 1-hydroxyethyl, aminosulfonyl, dimethylamino, or 2-(N,N-diethylamino)ethylamino.

DETAILED DESCRIPTION OF THE INVENTION

In the above formulas, "$C_1$–$C_4$ alkyl" means a straight or branched carbon chain such as methyl, ethyl, n-propyl, isobutyl, tert.-butyl, and the like. The alkyl group can be substituted with hydroxy, for example, 1-hydroxyethyl, 2-hydroxypropyl, 4-hydroxybutyl, "$C_1$–$C_4$ alkoxy-$C_2$–$C_4$ alkyl" are the foregoing $C_2$–$C_4$ alkyl groups having a similar alkyl substituent bonded through oxygen. Typical of such groups are 2-isopropoxyethyl, 3-methoxybutyl, and the like. The term "$C_3$–$C_6$ cycloalkyl" includes groups such as cyclopropyl, cyclobutyl, cyclohexyl, and the like.

In the above formula, $R^1$ and $R^2$ can be taken with the nitrogen to which they are attached to form a heterocyclic ring such as pyrrolidine, piperidine, morpholine, homopiperazine, and the like.

"Halo" in the above formulas includes fluoro, chloro, bromo, and iodo. Preferred halo groups are fluoro and chloro. $R^6$ and $R^7$ in the above formulas are substituents in either of the rings.

The compounds to be utilized as amyloid aggregation inhibitors are prepared as described in U.S. Pat. No. 3,218,309. For example, a diazonium compound of the formula

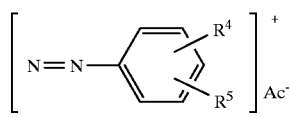

is reacted with an alpha-naphthylamine of the formula

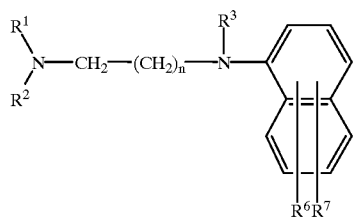

The naphthylazo compounds readily form salts with any of a number of common acids, for instance mineral acids such as hydrochloric acid, sulfuric acid, phosphoric acid, and organic acids such as oxalic, lactic, tartaric, malonic, and related acids.

The ability of the naphthylazo compounds of the above formulas to inhibit amyloid aggregation has been established in a standard in vitro assay. The assay is carried out by mixing beta amyloid peptide (1–40) with radioiodinated ($I^{125}$) labeled peptide to a concentration of 2.5 mg/mL in hexafluoroisopropanol. The mixure is diluted 1 to 5 with water (v/v). Ten milliliters of the solution is mixed with 25 $\mu$L of 25 mM sodium phosphate buffer pH 6.0. The mixture is allowed to aggregate for 2 hours at room temperature with and without a test compound present. The mixtures are then diluted to 235 $\mu$L with phosphate buffer to stop the aggregation process. The solutions are passed through a 0.2-$\mu$m millipore filtermat. Aggregated protein remains in the filter well. The filter plate is washed with 50 $\mu$L of phosphate buffer and then soaked in solid gel scintillant and counted on a Microbeta counter to determine the amount of aggregation in the presence of a test compound versus control with no test compound.

Several representative naphthylazo compounds have been evaluated and shown to inhibit amyloid aggregation. The following table presents the activity of selected compounds, reported as the molar concentration of compounds required to cause a 50% inhibition ($IC_{50}$) of amyloid aggregation in the above assay. Congo red exhibited an $IC_{50}$ of greater than 1000 $\mu$M in the test.

TABLE I

| $R^4$ | $R^5$ | $R^6$ | $R^7$ | $IC_{50}$ ($\mu$M) |
|---|---|---|---|---|
| H | Cl | H | H | 17.8 |
| H | H | H | H | 13.7 |
| -benzyloxy | H | H | H | 15.8 |
| —$SO_2NH_2$ | H | H | H | 7.0 |
| —OCH$_2$CH$_2$N(Et)(Et) | H | H | H | 10.5 |
| —NH—C(=O)—CH$_2$—S— | H | H | H | 16.1 |

TABLE I-continued

| R⁴ | R⁵ | R⁶ | R⁷ | IC₅₀ (μM) |
|---|---|---|---|---|
| —OCH₂CH₂OH | H | H | H | 18.6 |
| H | H | H | —OCH₂CH₂N(Et)(Et) | 9.9 |
| —NHCH₂CH₂N(Et)(Et) | H | H | H | 8.4 |
| —N(CH₃)(CH₃) | H | H | H | 14.4 |
| F | H | H | H | 34 |
| H | H | H | OCH₃ | 39 |
| H | H | OCH₃ | H | 17 |
| H | —CH(OH)—CH₃ | H | H | 30 |

For inhibition of amyloid aggregation according to this invention, all that is required is to administer to a mammal an effective amount of a naphthylazo compound as defined above. An "effective amount" as used herein is that quantity of naphthylazo compound which inhibits aggregation of amyloid protein without causing unacceptable toxic effects. Typical doses which are effective will be from about 0.1 to about 1000 mg/day, and more typically from about 50 to about 500 mg/day. The compounds can be administered from one to about three times a day for either prophylactic or therapeutic treatment of diseases related to the deposition of one or more amyloidogenic proteins, for example Alzheimer's disease, Down's syndrome, and in general advanced aging of the brain.

The naphthylazo compounds can be formulated for convenient administration orally or parenterally, for instance by intravenous or intramuscular routes. The compounds also are well suited to transdermal delivery, and can thus be formulated as patches, creams, lotions, and the like. Typical formulations for oral administration will be made by mixing the naphthylazo compound with common diluents and excipients such as corn starch, sugar, talc, and the like, and forming tablets, capsules, caplets, syrups, suspensions, and the like. For parenteral delivery, the compounds are ideally dissolved in isotonic saline or aqueous glucose for injection or intravenous delivery. The compounds can also be formulated with waxes and polymers and molded into suppositories or other common sustained-release delivery forms. The naphthylazo compounds are preferably converted to pharmaceutically acceptable salts to increase solubility and facilitate formulation and administration.

Because the naphthylazo compounds described above are also effective at binding to amyloids, they can additionally be utilized to detect amyloid deposition, and thus to detect disease states associated with amyloid aggregation, such as Alzheimer's disease.

The compounds can readily be radiolabeled with common radioisotopes such as $I^{125}$, tritium, or the like. For example, compounds wherein $R^4$ or $R^5$ are halo can be made with $I^{125}$. The radiolabeled compounds are synthesized employing common synthetic techniques utilizing readily available radioactive chemicals. The radiolabeled compound is then formulated and administered to a mammal in the same manner as described above for nonradiolabeled compounds. The mammal can then be scanned with common imaging sensors and equipment to detect amyloid deposition and aggregation.

We claim:

1. A method for inhibiting amyloid aggregation in a mammal comprising administering an effective amount of a compound having the formula

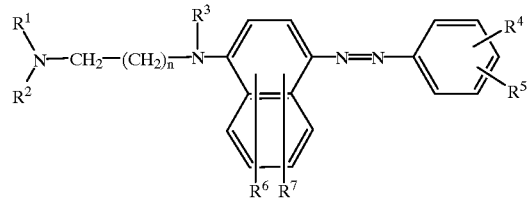

wherein:

$R^1$ and $R^2$ independently are hydrogen, $C_1-C_4$ alkyl, hydroxy $C_1-C_4$ alkyl, $C_1-C_4$ alkoxy-$C_2-C_4$ alkyl, $C_3-C_6$ cycloalkyl, or $R^1$ and $R^2$ taken together with the nitrogen to which they are attached complete a heterocyclic ring having from 4 to 12 carbon atoms;

n is 1, 2, or 3;

$R^3$ is hydrogen or $C_1-C_4$ alkyl;

$R^4$ and $R^5$ independently are hydrogen, hydroxy, halo, $C_1-C_4$ alkyl, $C_1-C_4$ alkoxy, phenoxy, benzyloxy, hydroxy-$C_1-C_4$ alkyl, hydroxy-$C_1-C_4$ alkoxy, $NR^1R^2$, $SO_2NR^1R^2$, $R^1R^2N-CH_2(CH_2)_n-(O$ or $NH)_m$ where $R^1$, $R^2$, and n are as defined above, and m is 0 or 1, and $R^4$ and $R^5$ when attached to adjacent carbon atoms can be

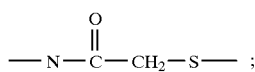

$R^6$ and $R^7$ independently are hydrogen, hydroxy, halo, $C_1-C_4$ alkyl, $C_1-C_4$ alkoxy, or $R^1R^2N-CH_2(CH_2)_n-(O$ or $NH)_m-$where $R^1$, $R^2$, m, and n are as defined above; and the pharmaceutically acceptable acid addition salts thereof.

2. The method according to claim 1 employing a compound having the formula

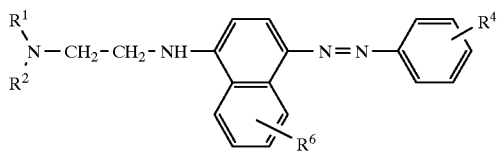

where $R^1$ and $R^2$ independently are $C_1-C_4$ alkyl and $R^4$ is hydrogen, halo, $SO_2NH_2$, benzyloxy, hydroxy $C_1-C_4$ alkyl, $NR^1R^2$, or $R^1R^2N-CH_2(CH_2)_n-(O$ or $NH)_m-$, and $R^6$ is hydrogen or $C_1-C_4$ alkoxy.

3. The method according to claim 2 employing a compound wherein $R^6$ is selected from $C_1-C_4$ alkoxy and $-OCH_2CH_2N(CH_2CH_3)_2$.

4. The method according to claim 3 employing a compound selected from:

N,N-diethyl-N'-[4-(phenylazo)-6-(2-N,N-diethylaminoethoxy)-1-naphthyl]-ethylenediamine;

N,N-diethyl-N'-[4-(phenylazo)-6-methoxy-1-naphthyl]ethylenediamine; and

N,N-diethyl-N'-[4-(phenylazo)-7-methoxy-1-naphthyl]ethylenediamine.

5. The method according to claim 1 employing a compound having the formula

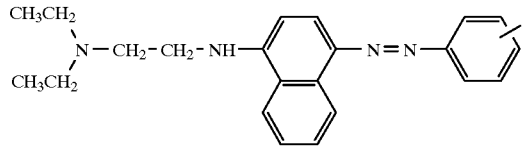

where $R^4$ is hydrogen, 3-chloro, 4-fluoro, benzyloxy, 2-(N,N-diethylamino)ethoxy, 2-hydroxyethoxy, 1-hydroxyethyl, aminosulfonyl, dimethylamino, or 2-(N,N-diethylamino) ethyl-amino.

6. The method according to claim 5 employing a compound selected from:

N,N-diethyl-N'-[4-(3-chlorophenylazo)-1-naphthyl] ethylenediamine;

N,N-diethyl-N'-[4-(4-fluorophenylazo)-1-naphthyl] ethylenediamine;

N,N-diethyl-N'-[4-(phenylazo)-1-naphthyl]-ethylenediamine;

N,N-diethyl-N'-[4-(4-benzyloxyphenylazo)-1-naphthyl] ethylenediamine;

N,N-diethyl-N'-[4-(4-aminosulfonylphenylazo)-1-naphthyl]ethylenediamine;

N,N-diethyl-N'-[4-(4-(2-N,N-diethylamino-ethoxy) phenylazo)-1-naphthyl]ethylenediamine;

N,N-diethyl-N'-[4-(4-(2-hydroxyethoxy)-phenylazo)-1-naphthyl]ethylenediamine;

N,N-diethyl-N'-[4-(4-(2-N,N-diethylamino-ethylamine) phenylazo)-1-naphthyl]ethylenediamine;

N,N-diethyl-N'-[4-(4-dimethylamino)-phenylazo)-1-naphthyl]ethylenediamine; and

N,N-diethyl-N'-[4-(3-(1-hydroxyethyl)-phenylazo)-1-naphthyl]ethylenediamine.

7. The method according to claim 1 wherein the amyloid aggregation occurs in a mammal having Alzheimer's disease.

8. A method of diagnosing a mammal having amyloid aggregation comprising administering an effective amount of a radiolabeled compound of the formula

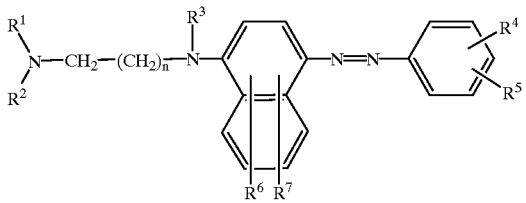

wherein:

$R^1$ and $R^2$ independently are hydrogen, $C_1-C_4$ alkyl, hydroxy $C_1-C_4$ alkyl, $C_1-C_4$ alkoxy-$C_2-C_4$ alkyl, $C_3-C_6$ cycloalkyl, or $R^1$ and $R^2$ taken together with the nitrogen to which they are attached complete a heterocyclic ring having from 4 to 12 carbon atoms;

n is 1, 2, or 3;

$R^3$ is hydrogen or $C_1-C_4$ alkyl;

$R^4$ and $R^5$ independently are hydrogen, hydroxy, halo, $C_1-C_4$ alkyl, $C_1-C_4$ alkoxy, phenoxy, benzyloxy, hydroxy-$C_1-C_4$ alkyl, hydroxy-$C_1-C_4$ alkoxy, $NR^1R^2$, $SO_2NR^1R^2$, $R^1R^2N-CH_2(CH_2)_n-(O$ or $NH)_m$ where $R^1$, $R^2$, and n are as defined above, and m is 0 or 1, and $R^4$ and $R^5$ when attached to adjacent carbon atoms can be

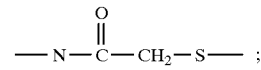

$R^6$ and $R^7$ independently are hydrogen, hydroxy, halo, $C_1-C_4$ alkyl, $C_1-C_4$ alkoxy, or $R^1R^2N-CH_2(CH_2)_n-(O$ or $NH)_m-$where $R^1$, $R^2$, m, and n are as defined above; and wherein at least one atom is radioactive, and the pharmaceutically acceptable acid addition salts thereof, and imaging the mammal to determine the accumulation of the compound in brain tissue.

* * * * *

UNITED STATES PATENT AND TRADEMARK OFFICE
CERTIFICATE OF CORRECTION

PATENT NO. : 5,955,472
DATED : Sep. 21, 1999
INVENTOR(S) : Hays et al.

Page 1 of 2

It is certified that error appears in the above-identified patent and that said Letters Patent is hereby corrected as shown below:

Column 7, line 54 delete

" 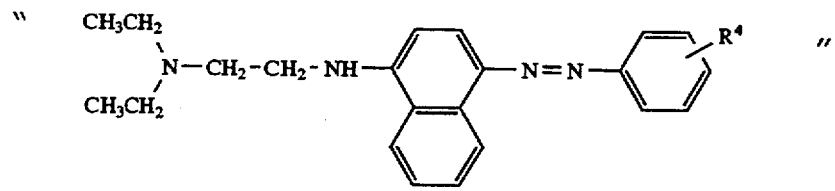 "

UNITED STATES PATENT AND TRADEMARK OFFICE
CERTIFICATE OF CORRECTION

Page 2 of 2

PATENT NO. : 5,955,472
DATED : Sep. 21, 1999
INVENTOR(S) : Hays, et al.

It is certified that error appears in the above-identified patent and that said Letters Patent is hereby corrected as shown below:

and insert

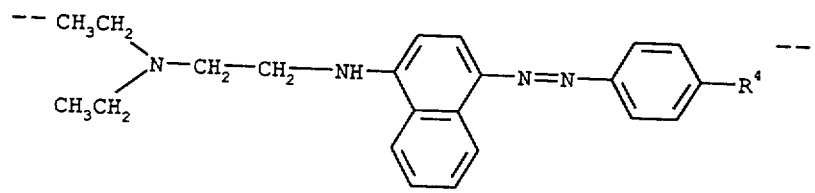

Signed and Sealed this

Eighteenth Day of April, 2000

Attest:

Q. TODD DICKINSON

Attesting Officer

Director of Patents and Trademarks